United States Patent [19]

Alam

[11] Patent Number: 5,981,552
[45] Date of Patent: Nov. 9, 1999

[54] SUBLINGUAL AND BUCCAL COMPOSITIONS OF DROPERIDOL AND METHOD FOR TREATING MIGRAINE

[75] Inventor: Abu Alam, Lake Forest, Ill.

[73] Assignee: Taylor Pharmaceuticals, Buffalo Grove, Ill.

[21] Appl. No.: 09/177,996

[22] Filed: Oct. 23, 1998

[51] Int. Cl.⁶ .................................................... A61K 31/44
[52] U.S. Cl. ............................................................ 514/338
[58] Field of Search ...................... 514/339, 338

[56] References Cited

U.S. PATENT DOCUMENTS

| | | | |
|---|---|---|---|
| 5,122,127 | 6/1992 | Stanley ................................. | 604/890.1 |
| 5,288,497 | 2/1994 | Stanley et al. .......................... | 424/440 |
| 5,310,561 | 5/1994 | Jao et al. ................................ | 424/465 |

OTHER PUBLICATIONS

Zhang et al., Pharmaceutical Research (New York), 14(11 Suppl.) S662 (abstract), 1997.

Steffens et al., Acta Anaesthesiologica 41 (Suppl. 110) 182 (abstract), 1997.

Wang, et al. Droperidol Treatment of Status Migrainosus and Refractory Migraine, Headache. Jun., 1997, pp. 377–382.

Wang, et al. Droperidol Treatment of Acute Refractory Migraine and Status Migrainosus, Headache, Apr., 1996, p. 280.

John F. Rothrock, MD., Treatment of Acute Migraine with Intravenous Droperidol, Headache, Apr. 1997, pp. 256–257.

*Primary Examiner*—Phyllis G. Spivack
*Attorney, Agent, or Firm*—Leydig, Voit & Mayer, Ltd.

[57] ABSTRACT

Sublingual and buccal dosage forms of droperidol are provided in a method for treating migraine using such formulations.

9 Claims, No Drawings

SUBLINGUAL AND BUCCAL COMPOSITIONS OF DROPERIDOL AND METHOD FOR TREATING MIGRAINE

FIELD OF THE INVENTION

This invention relates to the field of migraine treatment.

BACKGROUND OF THE INVENTION

The prevalence of migraine is said to be approximately 6% of the male population and 18% of the female population. Treatment for many patients having the occasional migraine usually involves simple analgesics, non-steroidal anti-inflammatory agents, or specific agents such as ergotamines or triptans. Approximately 10% of migraine sufferers have three or more attacks per month and warrant prophylactic treatment. Preventative agents such as beta-blockers, tricyclic antidepressants and divalproex sodium can reduce but not eliminate migraine attacks in some patients. Thus, there remains a need for migraine specific medications such as sumatriptan. In the remaining population of migraine sufferers, and in those with intolerable side-effects from available drugs, there is a lack of conventional pharmaceutical preparations that exhibit therapeutic effect, without severe side-effects.

Droperidol presently is marketed by Taylor Pharmaceuticals under the trademark Inapsine, as an injectable formulation used in anesthesia for preoperative surgery. It has never been approved for use in the treatment or management of migraine attacks.

A limited, uncontrolled, non-blinded, use of droperidol lactate (2.5 mg/ml droperidol) to treat migraine attacks was attempted and the results published in *Headache*, April 1996, p.280. In that publication it was reported that 20 patients received from 2.5 to 7.5 mg droperidol intravenously, in increments of 2.5 mg every 30 minutes until the patient was headache free or until a total of three doses had been administered. The mean dose was 5.6 mg. All of the patients received prior treatment with migraine therapies. Eighteen of the patients reported to be headache-free by the last dose. Although the article reports on apparently encouraging results in treating migraine attacks with droperidol, no definitive conclusions can be reached from the results reported in that article as the number of patients treated was small, the study was not blinded, all patients received other agents to treat the migraine episode prior to receiving droperidol, and there was no placebo control. Also, there was no attempt to repeat the results with the patients. Further, no attempt was made to prolong therapy beyond the initial treatment to a headache-free state and most patients had continuing symptoms to some degree within 24 hours after the last droperidol treatment.

Additionally, the aforementioned study and article only used intravenous droperidol. Others also have used intramuscular droperidol in uncontrolled, open studies for treatment of migraine of varying dose levels of droperidol. The use of droperidol by injection raises several issues, not the least of which is inconvenience to the patient, caused by the need to have the droperidol administered by a health care professional.

Accordingly, a need exists for a means to treat patients who suffer from, or are at risk of, a migraine episode, that does not require the use of injections of droperidol.

SUMMARY OF THE INVENTION

In accordance with the present invention, droperidol is supplied in a dosage form that provides better patient tolerance and improved ease of administration. In particular, the present invention relates to the use of sublingual and buccal dosage forms of droperidol.

The dosage forms of the present invention comprise sublingual tablets and solution compositions that are administered under the tongue and buccal tablets that are placed between the cheek and gum.

The dosage forms of the present invention may be used to treat migraine episodes, by administration to a patient during a migraine attack, in an amount that is effective to treat symptoms of migraine. The dosage forms of droperidol may be used without pretreatment or in conjunction with other migraine therapies.

The dosage forms of the present invention also may be used to treat patients that are suffering from tension headache, vertigo, or hyperemesis gravidarum. The dosage forms also may be used as antiemetics, to treat nausea and the like, such as that caused by chemotherapy. In each instance the dosage is administered in an amount sufficient to treat the patient's symptoms.

The present invention also provides sublingual and buccal dosage forms of droperidol that comprise from 0.1 to 10 mg of droperidol per unit dosage.

DETAILED DESCRIPTION OF THE PREFERRED EMBODIMENTS

The present invention provides dosage forms of droperidol containing various amounts of droperidol, such as between about 0.1 and 10 mg droperidol per unit dosage, such as tablets and solutions, that are particularly useful. Typically the dosage will be 2 to 4 mg.

The droperidol may be present as the lactate, or any other suitable organic salts of droperidol may be used, such as tartrate, acetate or citrate.

As indicated, patients that are suffering from a migraine episode, tension headache, vertigo, hyperemesis gravidarum, or nausea may be treated. The patients are administered the droperidol, typically in dosages of 1 mg to 10 mg, until the symptoms subside. The maximum dosage of droperidol administered to a patient at a single session usually will be 10 mg.

The patients receiving droperidol to treat migraine may be treated with droperidol as a single therapy. By this it is meant that other agents used to treat an active episode of migraine need not be used prior to or in conjunction with the droperidol treatment. Many patients receive various medications for prophylaxis against active migraine episodes, but such prophylactic therapy is not considered to be pretreatment of an active migraine episode, prior to droperidol treatment. Such therapy is nonspecific in that the goal is to prevent or reduce the number of occurrences of active migraine headache, but not the treatment of a specific migraine episode. The present dosage forms will be useful as a first-line treatment of active migraine headache without the prior use of traditional migraine therapy, or as a rescue medication when other treatment has failed.

Presently, an active migraine episode may be treated with any of a number of therapies, including the following: Simple analgesics, such as aspirin or acetaminophen, combination analgesics as with caffeine, vasoconstrictors, narcotics, and the like.

As indicated, the use of droperidol in accordance with the present invention does not require the prior administration of such other agents for treating migraine.

The migraine patients to whom droperidol should be administered are those that are experiencing a migraine episode or are at risk of such an episode. Such patients may be generally described as those meeting the diagnostic criteria for "migraine with aura" or "migraine without aura" as detailed in: "Classification Committee of the International Headache Society. Classification and Diagnostic Criteria For Headache Disorders, Cranial Neuroalgia and Facial Pain", *Cephalgia*, 1988, Vol. 8, Supp. 77 at pp. 19–21; or meeting the diagnostic criteria for "status migrainosus", as detailed therein at pp. 26–27.

For some patients it may be beneficial to administer an additional dose of droperidol after the headache has subsided to reduce the probability that the headache will return in a short period of time. Such an additional dose of droperidol may be used to avoid the use of a sedative or other analgesics within the next few hours after the headache symptoms have subsided. Presently it is typical for patients, after they have been rendered headache-free, to resort to such remedies as sedation or use of analgesics shortly after the headache symptoms have subsided to reduce the recurrence of the migraine symptoms after the patient has become headache-free. The present invention may avoid the need for such remedies.

Sublingual and buccal delivery allows droperidol to dissolve in the immediate vicinity where the product is placed and then the drug enters directly into the blood stream to exert its pharmacological effect rapidly. Thereby, by-passing the gastric juices, acid environment and enzymes present in the gastrointestinal tract and at the same time by-passing the liver which is the target organ for metabolism of the drug when administered orally. The highly vascular mucosal lining between the cheek and gum where buccal tablets are placed or under the tongue where sublingual tablets or solutions are placed are ideal and convenient locations for the droperidol to be absorbed. Moreover, the smaller total dose of droperidol ranging from 0.5 to 10 mg for therapeutic effect also lends itself for effective dosage design by the sheer physical size.

SUBLINGUAL TABLETS

In order to form in tablets, there are used carriers such as vehicles (e.g. lactose, white sugar, mannitol, glucose, starches, calcium carbonate, crystalline cellulose, silicic acid, etc.), binders (e.g. water, ethanol, myranol, glucose solution, starch solution, gelatin solution, polyvinylpyrrolidone, etc.), disintegrators (e.g. dry starch, sodium, alginate, sodium hydrogen carbonate, calcium carbonate, polyoxyethylene sorbitan fatty acid esters, sodium laurylsulfate, stearic monoglyceride, starches, lactose, etc.), absorption promoters (e.g. quaternary ammonium base, sodium laurylsulfate, etc.), wetting agents (e.g. glycerin, starches, etc.), lubricants (e.g. stearates, polyethylene glycol, etc.), and the like. Moreover, the tablets may be in the form of a conventional tablet, or a molded tablet.

BUCCAL TABLETS

In order to formulate into tablets, various carriers and excipients are used to offer the acceptable characteristics such as: lactose, sugar, mannitol, acacia, providone, cyclodextrins, hydroxypropylmethylcellulose, ethylcellulose, methylcellulose, sodium carboxymthylcellulose, microstrystalline cellulose, Carbapol 934, stearic acid, magnesium stearate, locust bean gum, xanthan gum, water, alcohol, isopropanol and artificial flavoring and sweetening agents.

SOLUTIONS

In order to formulate into solutions, various carriers, excipients, pH adjusters are employed such as: water, sugar, lactic acid, acetic acid, fructose, glucose, saccharin, polyethylene glycol, propylene glycol, alcohol, bentonite, tragacanth, gelatin, alginates, aspartame, sorbitol, methylparaben, propylparaben, sodium benzoate, artificial flavoring and coloring agents.

The present invention will be described in terms of the following non-limiting examples:

EXAMPLE 1

Sublingual Tablet Formulation

| Ingredient | 0.1 mg/Tablet | 10 mg/Tablet |
|---|---|---|
| Droperidol | 0.1 mg | 10 mg |
| Mannitol | 5 mg | 10 mg |
| Microcrystalline cellose | 20 mg | 20 mg |
| Magnesium stearate | 0.1 mg | 0.1 mg |
| Total Weight/Tablet: | 25.2 mg | 40.1 mg |

Tablet Process: The ingredients of 1,000 tablets (25.6 g for 0.1 mg formulation and 40.1 g for 10 mg formulation) are blended in a suitable mixer and then compressed into tablets. Tablets are packaged into bottles or individual blister strips.

EXAMPLE 2

Sublinaual Tablet Formulation

| INGREDIENT | 0.1 mg/Tablet | 10 mg/Tablet |
|---|---|---|
| Droperidol | 0.124 mg* | 12.4 mg** |
| Sucrose | 30.0 mg. | 30.0 mg |
| Magnesium Stearate | 0.106 mg | 0.2 mg |
| Total Weight/Tablet: | 30.23 mg | 42.6 mg |

*0.1 mg. Droperidol = 0.124 mg Droperidol Lactate
**10 mg Droperidol = 12.4 mg Droperidol Lactate Tablet Process: The ingredients of 1,000 tablets (30.23 g for 0.1 mg formulation and 42.6 g for 10 mg formulation) are blended in a suitable mixer and then compressed into tablets. Tablets are packaged into bottles or individual blister strips.

EXAMPLE 3

Buccal Tablet Formulation

| INGREDIENT | 0.1 mg/Tablet | 10 mg/Tablet |
|---|---|---|
| Droperidol | 0.1 mg | 10 mg |
| Spray Dried Lactose | 10 mg | 20 mg |
| Hydroxypropylmethylcellulose | 20 mg | 30 mg |
| Sucrose | 10 mg | 10 mg |
| Taragacanth | 5 mg | 10 mg |
| Magnesium stearate | 0.3 mg | 0.5 mg |
| Total Weight/Tablet | 45.4 mg | 80.5 mg |

Tablet Process: The ingredients of 1,000 tablets (45.4 g of the 0.1 mg formulation and 80.5 g of the 10 mg formulation) are blended in a suitable mixer and compressed into tablet by using flat faced punches and die. The tablets are filled into bottles or individual blister strips.

EXAMPLE 4

Sublinaual Solution Formulation

| INGREDIENT | 0.1 mg/0.1 ml | 10 mg/0.5 ml |
|---|---|---|
| Droperidol | 0.1 mg | 10 mg |
| Lactic acid qs. to pH | 3.5 | 3.5 |
| Citrus flavor | 0.1 mg | 0.2 mg |
| Sucrose | 10 mg | 15 mg |
| Sodium benzoate | 0.1 mg | 0.2 mg |
| Water qs. ad. | 0.1 ml | 0.5 ml |
| Total Weight: | 0.1 ml (0.1 g) | 0.5 ml (0.5 g) |

Solution process: In a suitable vessel, droperidol is dissolved with lactic acid with pH adjusted to about 3.5 in sufficient quantity of water. The remaining ingredients are then added and dissolved. Sufficient water is then added for 1,000 units (100 ml for 0.5 mg formulation and 500 ml for 10 mg formulation). The solution is filtered and put into bottles equipped with a dropper to allow the solution to be placed accurately under the tongue. The filtered solution can also be packaged into bottles with a metered spray to allow accurate dosing under the tongue.

What is claimed:

1. A method for treating a patient suffering from a migraine episode or tension headache, comprising sublingually or buccally administering droperidol to the patient, in an amount that is effective to treat said symptoms, said amount being from about 0.1 mg to about 10 mg.

2. The method of claim 1 wherein the droperidol is present as an lactate salt.

3. The method of claim 1 wherein the droperidol is present as a tartrate salt.

4. The method of claim 1 wherein the droperidol is present in an acetate salt.

5. The method of claim 4 wherein the dose of droperidol is in the range of about 1 mg to about 10 mg.

6. The method of claim 1 wherein the droperidol is present in a sublingual tablet.

7. The method of claim 1 where the droperidol is present in a sublingual solution.

8. The method of claim 1 wherein the droperidol is present in a buccal tablet.

9. The method of claim 1 where the dose is from about 2 to about 4 mg.

* * * * *